United States Patent
Barkan et al.

(10) Patent No.: US 10,916,343 B2
(45) Date of Patent: Feb. 9, 2021

(54) REDUCE DISCREPANCY OF HUMAN ANNOTATORS IN MEDICAL IMAGING BY AUTOMATIC VISUAL COMPARISON TO SIMILAR CASES

(71) Applicant: International Business Machines Corporation, Armonk, NY (US)

(72) Inventors: Ella Barkan, Haifa (IL); Alon Hazan, Zikhron Yaakov (IL); Vadim Ratner, Haifa (IL)

(73) Assignee: International Business Machines Corporation, Armonk, NY (US)

( * ) Notice: Subject to any disclaimer, the term of this patent is extended or adjusted under 35 U.S.C. 154(b) by 237 days.

(21) Appl. No.: 15/963,120

(22) Filed: Apr. 26, 2018

(65) Prior Publication Data

US 2019/0333625 A1    Oct. 31, 2019

(51) Int. Cl.
*G16H 30/40* (2018.01)
*G16H 30/20* (2018.01)
*G06F 16/58* (2019.01)

(52) U.S. Cl.
CPC ........... *G16H 30/40* (2018.01); *G16H 30/20* (2018.01); *G06F 16/5866* (2019.01)

(58) Field of Classification Search
CPC .................................................. G16H 30/20
See application file for complete search history.

(56) References Cited

U.S. PATENT DOCUMENTS

| | | | |
|---|---|---|---|
| 2008/0052126 A1* | 2/2008 | Sasai | G06F 19/321 705/3 |
| 2016/0300120 A1 | 10/2016 | Haas et al. | |
| 2017/0091413 A1 | 3/2017 | Kondo et al. | |
| 2017/0300621 A1 | 10/2017 | Lee | |
| 2017/0337328 A1* | 11/2017 | Ruppertshofen | G16H 30/20 |

OTHER PUBLICATIONS

Goede et al., "A Methodology and Implementation for Annotating Digital Images for Context-appropriate Use in an Academic Health Care Environment", Journal of the American Medical Informatics Association, Jan.-Feb. 2004, pp. 29-41, vol. 11, Issue 1.
Iakovidis et al., "Ratsnake: A Versatile Image Annotation Tool with Application to Computer-Aided Diagnosis", The Scientific World Journal, 2014.

\* cited by examiner

*Primary Examiner* — Sheetal R Paulson
(74) *Attorney, Agent, or Firm* — Dvir Gassner (57) ABSTRACT

A method comprising using at least one hardware processor for automatically receiving, using a user interface associated with the hardware processor(s), an annotation for a medical image of a patient, the medical image associated with a suspected disease of the patient and metadata of the patient. The hardware processor(s) are configured for performing a search query in real time on a database for the annotation. The hardware processor(s) are configured for receiving at least one result of the search query. The hardware processor(s) are configured for retrieving at least one other medical image comprising at least one other annotation, wherein the at least one other medical image is associated with the at least one result. The hardware processor(s) are configured for displaying, on the user interface, the at least one other medical image and the at least one other annotation.

13 Claims, 4 Drawing Sheets

REDUCE DISCREPANCY OF HUMAN ANNOTATORS IN MEDICAL IMAGING BY AUTOMATIC VISUAL COMPARISON TO SIMILAR CASES

BACKGROUND

The invention relates to the field of medical imaging.

When a subject is treated by a physician for symptoms of a particular disease, the treating physician may order one or more medical imaging acquisitions (i.e. scans) to further diagnose the disease that is causing the symptoms. Radiologists review medical images of a subject (i.e. a case) and produce a textual radiologist report with the radiographic findings seen in the images. The review process may involve annotating the medical images, such as describing what the radiologist sees, what the radiologist considers abnormal in the image, measuring objects in the images (such as distances, angles, volumes, and/or the like), pointing out features of the images, setting keywords to the objects, and/or the like. The radiographic findings are typically the differences between the subject's images and what the radiologist considers to be the normal appearance expected of these images. This knowledge is based on years of training during the radiologist specialization studies. The radiologist report is sent to the treating physician for further medical treatment of the patient, when needed.

Computer aided diagnosis (CAD) systems may assist radiologists read new images by showing them similar cases (but not similar annotation) from the database, however this may not be a medical image annotation process and CAD systems may assume a single true lexicon for annotations which is may not be practical.

The foregoing examples of the related art and limitations related therewith are intended to be illustrative and not exclusive. Other limitations of the related art will become apparent to those of skill in the art upon a reading of the specification and a study of the figures.

SUMMARY

The following embodiments and aspects thereof are described and illustrated in conjunction with systems, tools and methods which are meant to be exemplary and illustrative, not limiting in scope.

There is provided, in accordance with an embodiment, a method comprising using at least one hardware processor for automatically receiving, using a user interface associated with the at least one hardware processor, an annotation for a medical image of a patient, the medical image associated with a suspected disease of the patient and metadata of the patient. Hardware processor(s) are configured for performing a search query in real time on a database for the annotation. Hardware processor(s) are configured for receiving at least one result of the search query. Hardware processor(s) are configured for retrieving at least one other medical image comprising at least one other annotation, wherein the at least one other medical image is associated with the at least one result. Hardware processor(s) are configured for displaying, on the user interface, the at least one other medical image and the at least one other annotation.

Optionally, the method further comprises the actions of: (i) receiving at least one new annotation for at least one of the medical image and the at least one other medical image, and (ii) storing the at least one new annotation in the database.

There is provided, in accordance with an embodiment, a computer program product for automatically comparing annotations of medical images. The computer program product comprising a non-transitory computer-readable storage medium having program code embodied therewith. The program code is executable by at least one hardware processor to automatically receive, using a user interface associated with the at least one hardware processor, an annotation for a medical image of a patient, the medical image associated with a suspected disease of the patient and metadata of the patient. The program code is executable by at least one hardware processor to automatically perform a search query in real time on a database for the annotation. The program code is executable by at least one hardware processor to automatically receive at least one result of the search query. The program code is executable by at least one hardware processor to automatically retrieve at least one other medical image comprising at least one other annotation, wherein the at least one other medical image is associated with the at least one result. The program code is executable by at least one hardware processor to automatically display, on the user interface, the at least one other medical image and the at least one other annotation.

Optionally, the computer program product is further configured for: (i) receiving at least one new annotation for at least one of the medical image and the at least one other medical image, and (ii) storing the at least one new annotation in the database.

There is provided, in accordance with an embodiment, a system comprising a non-transitory computer-readable storage medium having program code embodied therewith and at least one hardware processor configured to execute the program code. The program code is executable by at least one hardware processor to receive, using a user interface associated with the at least one hardware processor, an annotation for a medical image of a patient, the medical image associated with a suspected disease of the patient and metadata of the patient. The program code is executable by at least one hardware processor to perform a search query in real time on a database for the annotation. The program code is executable by at least one hardware processor to receive at least one result of the search query. The program code is executable by at least one hardware processor to retrieve at least one other medical image comprising at least one other annotation, wherein the at least one other medical image is associated with the at least one result. The program code is executable by at least one hardware processor to display, on the user interface, the at least one other medical image and the at least one other annotation.

Optionally, the system is further configured for: (i) receiving at least one new annotation for at least one of the medical image and the at least one other medical image, and (ii) storing the at least one new annotation in the database.

Optionally, the database is incorporated into at least one of a picture archiving and communication system (PACS) system and a radiological information system (RIS) system.

Optionally, the search query is a Digital Imaging and Communications in Medicine (DICOM) search query, and the retrieving is performed using a DICOM retrieve command.

Optionally, the annotation and the at least one other annotation each comprise at least one of a plurality of text annotations.

Optionally, the annotation and the at least one other annotation each comprise at least one of a plurality of graphic annotations.

Optionally, the search query further comprises searching for at least one of: the medical image, the suspected disease, and the metadata.

In addition to the exemplary aspects and embodiments described above, further aspects and embodiments will become apparent by reference to the figures and by study of the following detailed description.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. The figures are listed below.

DETAILED DESCRIPTION

Disclosed herein are a method, system, and computer program product to reduce the discrepancy between different human annotators (i.e. radiologists) of imagery and even between the same annotator at different times. During the process of annotating medical images, the self-discrepancy and mutual-discrepancy of nomenclature in describing objects (such as round, oval, homogeneous, irregular, etc.) may be greatly reduced by presenting the annotator (i.e. radiologist) with similar cases in a real-time, automatic, dynamic, single-view method, according to present embodiments.

For example, during the annotation process of a specific case the annotator decides to label a tumor as "homogeneous", "irregular shaped", "indistinct margin", etc. During the annotation process, the technique will automatically and dynamically search previous cases in the memory, such as in a database, and match the cases to the current one based on the annotations, patient, suspected disease, etc. The matched cases may be displayed on the screen next to the current case images. This side by side comparison of annotations, may allow the annotator to immediately observe discrepancies between the current case and previous cases that are similar. When there is a discrepancy, the annotator may adjust the annotations of the current case and/or adjust the stored annotations of the auto-displayed cases from the database.

The disclosed technique encourages annotations to conform to a more precise interpretation of the abstract semantics, conform to medical standards, reduce variability in labels, improve the consistency of the database, and/or the like.

One technical problem solved by the invention is the discrepancy between different human annotators (i.e. radiologists) and even between the same annotator at different times. For example, a radiologist may annotate the medical image depicting a tumor during a first visit of a patient with an annotation of "rough edges" and annotate a second image depicting the same tumor during a second visit with the annotation of "incoherent edges". The causes for this example discrepancy may be that: medical imaging annotation semantics may be used ad-hoc, the medical field advances with new terminology, the practices at different radiology departments may change over time or across locations, and/or the like. Often, annotator judgment and experience may assist in consistent annotations, yet even between highly experienced radiologists there may be differences in annotations due to subjective decisions of the meaning of words such as "round", "oval", "heterogeneous", "medium density", etc. in the context of medical images. Those differences in the meaning of annotation words may result in variability of semantic labels in the annotation process and may further result in challenges to computer-based machine learning algorithms that are unable to find proper rules for classification due to the high annotation variability. The techniques of the present disclosure offer solutions to this problem be presenting a constant visual reminder to the radiologist of possible suitable annotations.

Figure 1:
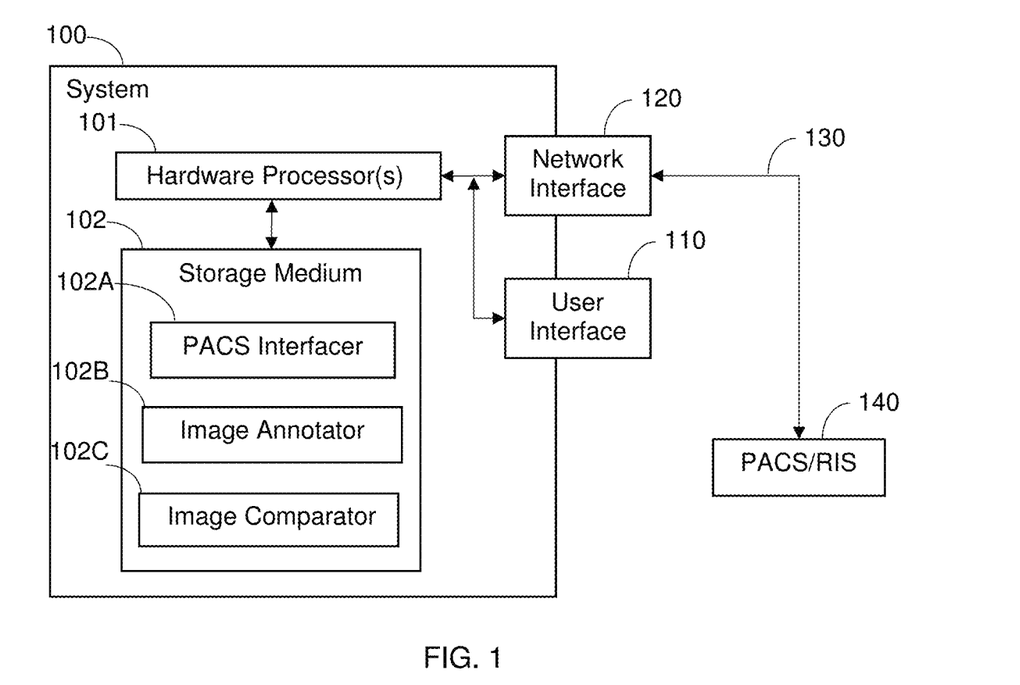
FIG. 1 shows schematically a system for medical image annotation consistency.
Figure 2:
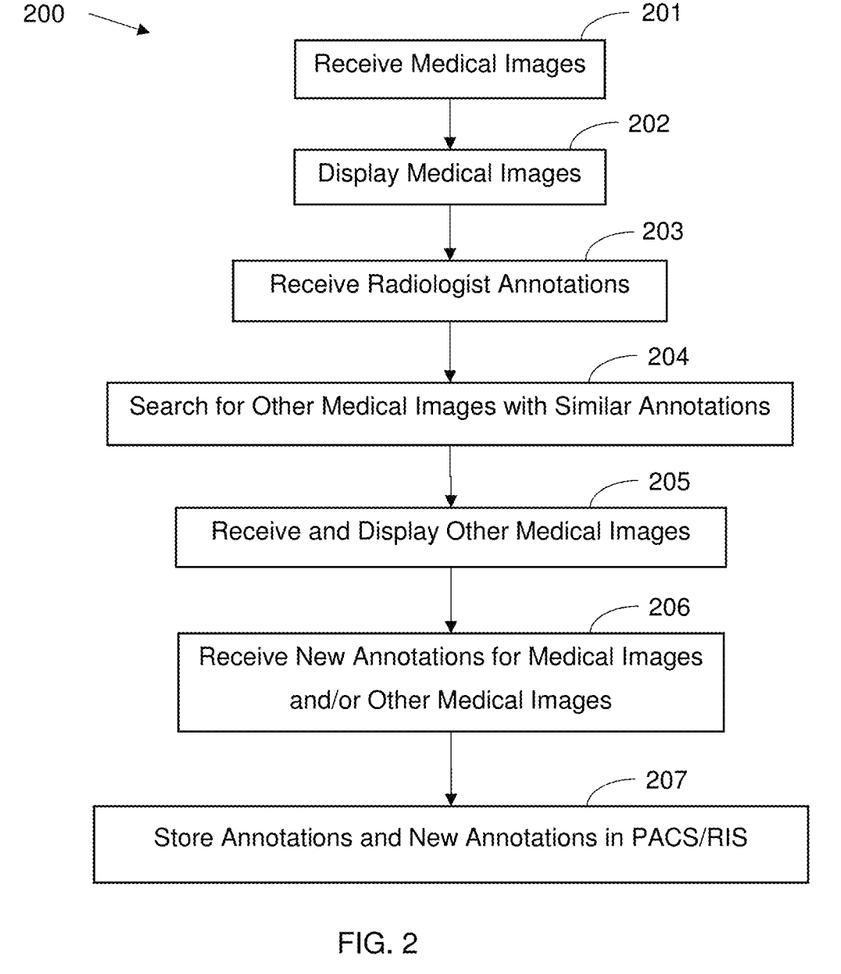
FIG. 2 shows a flowchart of a method for medical image annotation consistency.

Reference is now made to FIG. 1, which shows schematically a system 100, and to FIG. 2, which shows a flowchart 200 of a method, both drawings for medical image annotation consistency. System 100 comprises one or more hardware processors 101, a non-transitory computer-readable storage medium 102, a user interface 110, and a network interface 120. Network interface 120 is connected to a network 130 for communication with a medical image database 140, such as a picture archiving and communication system (PACS). Storage medium 102 has encoded thereon program code comprising processor instructions. When the specific processor instructions disclosed are executed on hardware processor(s) 101, hardware processor(s) 101 is configured to execute certain non-conventional actions. As such, the program code is said to be configured to instruct actions on hardware processor(s) 101, such as by a software module.

PACS Interfacer 102A is configured to receive 201 medical images and display 202 the medical images on user interface 110. A radiologist reads the medical images for a suspected disease attributed to the patient. The medical images were acquired using an imaging modality, such as magnetic resonance imaging, computed tomography, digital radiology, computed radiography, ultrasound imaging, and/or the like. The radiologist may annotate 203 the medical images, such as using Image Annotator 102B tools incorporated into system 100, workstation tools, PACS tools, and/or the like. The annotations, medical images, suspected disease, patient information, and/or the like, are used to search 204 for other medical images to display 205 to the radiologist on user interface 110. For example, Image Annotator 102B may be configured to issue a search query in real time to the database, the search query configured to find similar annotations, medical images, suspected disease, patient information, and/or the like. An Image Comparator 102C may be configured to receive and display 205 the other medical images in real time, such as images of similar cases. Image Annotator 102B may be configured to receive 206 new annotations for the medical images and/or other medical images, and store 207 the annotation and/or new annotations in a database, such as a PACS and/or radiology information system (RIS).

A search for other medical images, similar to the medical images being read by the radiologist (i.e. current case), may be performed by an automatic real-time search query to a database of images, image annotations, patient information, disease information, a hierarchal medical lexicon, and/or the like. For example, a Digital Imaging and Communications in Medicine (DICOM) query is sent in real time to the PACS system, such as a C-FIND DICOM query for annotations used as part of the DICOM images stored on the PACS. For example, the DICOM PS3.3 2018a—Information Object Definitions standard published by the National Electrical Manufacturers Association (NEMA), in Part 3, Section C.10.5, defines Graphic Annotation Module Attributes. For example, DICOM attribute Text Object Sequence, i.e. tag number (0070,0008), may contain text data, that when searched for using the C-FIND DICOM query may be retrieved in real time by Image Comparator 102C with a C-GET DICOM query command. Optionally, a search query uses attribute Graphic Annotation Sequence, i.e. tag number (0070,0001), to find graphic and/or text annotations. For example, a query in real time to a RIS system may be used to retrieve in real time (and automatically) the other medical images used to compare annotations. For example, an automatic query to a generic database system in real time may be used to retrieve in real time the other medical images used to compare annotations.

Optionally, a prioritizing score is used to prioritize (i.e. rank) the similar cases retrieved automatically in real time from the database, such as based on patient disease severity, visual similarity between images and/or graphic annotations, textual similarity between patient metadata and/or annotations, and/or the like. For example, the prioritizing score is used to rank the search results and determine which results should be displayed and compared to the current case, such as the similar cases retrieved based on elements of the annotations, and/or the like. For example, a severity(x) function may be a set of scores that are higher when the severity changes significantly (i.e. having different severities), such as severity(irregular:oval)=5. For example, a visual(x) function may be a set of scores that are lower when objects are visually similar, such as visual(oval:round)=1. For example, a prioritizing score may be:

$$\text{prioritizing score} = \frac{\sum_i \text{severity}(x_i)}{\sum_i \text{visual}(x_i)}$$

where the index i denotes all the characteristics found in the similar cases (i.e. shape, margin, density, distribution, etc.) and the sum is of all characteristic scores.

Optionally, the prioritizing score is defined in different ways. For example, a prioritizing score may depend only on $\Sigma_i \text{visual}(x_i)$ or only on $\Sigma_i \text{severity}(x_i)$ and not the combination of them (such as dependent upon the needs of the specific modality). For example, the prioritizing score shows the visually closest lesions that are not identical, which mathematically means $\min\{\Sigma_i \text{visual}(x_i)\}$ such that $\Sigma_i \text{visual}(x_i) > 0$. For example, the prioritizing score is defined as linear combinations of severity(x) and visual(x). For example, the prioritizing score is defined as combinations of powers of severity(x) and visual(x). For example, the prioritizing score is the sum of some, but not all, of the functions of the characteristics (i.e. top-k characteristics).

Optionally, tables are used to determine function values. For example, the following table shows some visual function values:

TABLE 1

Ultrasound (US) Margins for visual function values

| US Margin | indistinct | circumscribed | Microlobulated | spiculated |
|---|---|---|---|---|
| indistinct | 0 | 1 | 0.5 | 0.2 |
| circumscribed | 1 | 0 | 0.7 | 1 |
| microlobulated | 0.5 | 0.7 | 0 | 0.7 |
| spiculated | 0.2 | 1 | 0.7 | 0 |

TABLE 1 describes the visual similarity of the margin characteristic of masses (i.e. tumors) in ultrasound images. Similar tables may be defined for other modalities, i.e. CT, MRI, and and/or the like. TABLE 1 defines a score of how visually different 2 lesions are based on their margin. For example, a spiculated lesion is not so different (visual score=0.2) from an indistince lesion. But very different (visual score=1) from a circumscribed lesion.

Similarly, another table may define severity values for the prioritizing score. This table may be a higher dimension table, to cover many possible permutations of characteristics, for example characteristics may include those in the following table:

TABLE 2

Ultrasound (US) Margins for severity function values

| Severity value | Characteristics |
|---|---|
| 0 | oval, circumscribed, low density |
| 0.02 | oval, circumscribed, medium density |
| ... | |
| 1 | irregular, spiculated, high density |

For example, if the annotator has currently defined a lesion as "oval, circumscribed, medium density" then it has severity of 0.02 so showing him a lesion that is "oval, circumscribed, low density" will be −0.02 in severity distance and showing a lesion that is "irregular, spiculated, high density" is 0.98 in severity distance.

Figure 3:
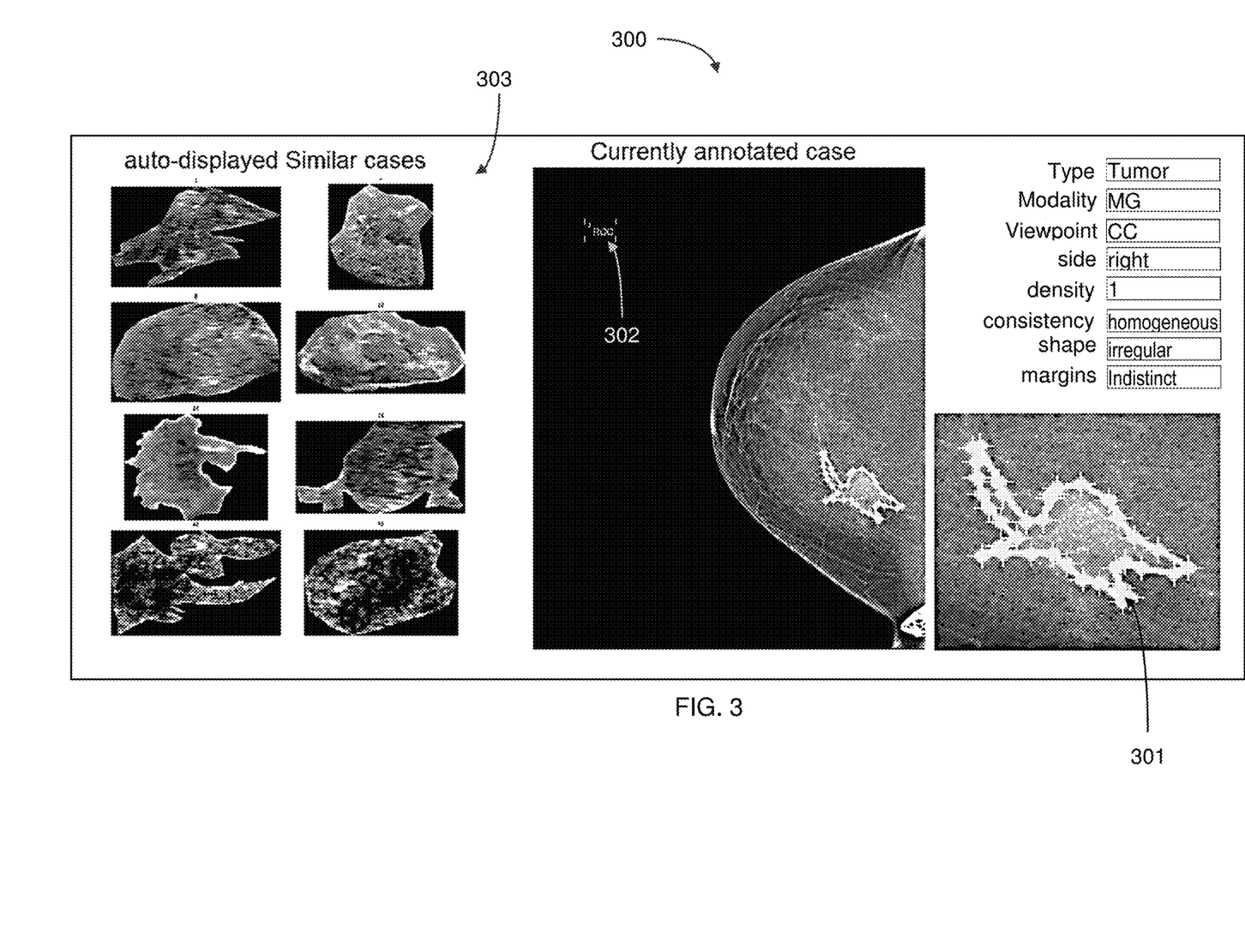
FIG. 3 shows a first screen image of a user interface for medical image annotation consistency.

Reference is now made to FIG. 3, which shows a first screen image 300 of a user interface for medical image annotation consistency. For example, screen 300 shows the current case being annotated 302 in the center of screen 300, and a zoomed area 301 on the right side. For example, a radiologist labels the tumor, using user interface 110 (FIG. 1), according to a subjective interpretation of the semantics. During the annotation process, Image Annotator 102B (FIG. 1) automatically searches 204 (FIG. 2) in real time for similar cases (i.e. other medical images) based on the annotations, machine-based similarity of the medical images, patient information, suspected disease, and/or the like. The medical images of the similar cases may appear on the left side 303 of screen 300 so the radiologist may easily and naturally compare the images and/or annotations of the similar other cases to the current case.

Figure 4:
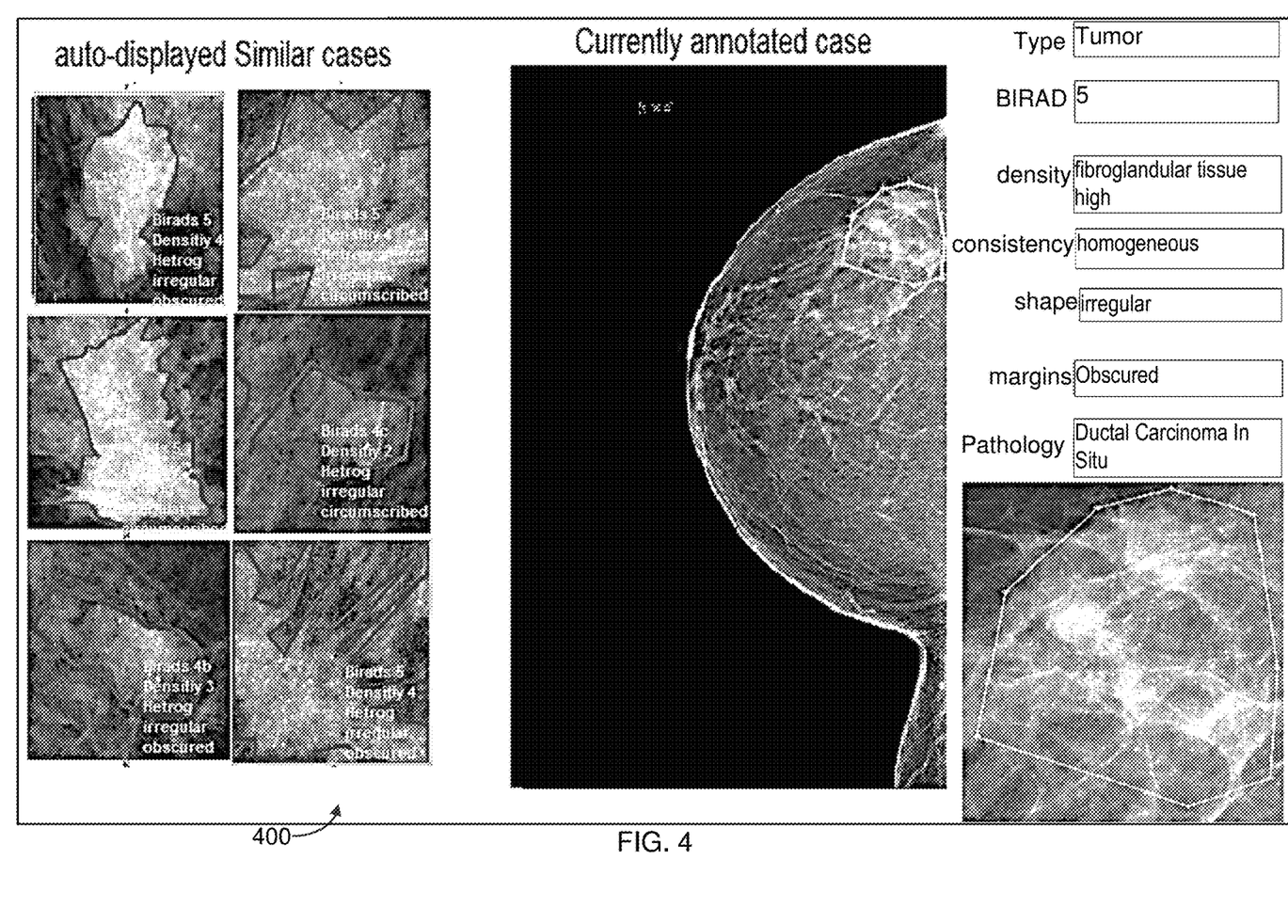
FIG. 4 shows a second screen image of a user interface for medical image annotation consistency.

Reference is now made to FIG. 4, which shows a second screen image 400 of a user interface for medical image annotation consistency. As seen in FIG. 3, the other medical images and other medical annotations on the left side of screen 400 automatically assist the radiologist in real time to selecting annotations for the current case. For example, as the radiologist changes the annotation of the current case, the samples from the other medical images change interactively in real time, and the radiologist may finish modifying the annotations of the current case once the other medical images match the current case.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire. Rather, the computer readable storage medium is a non-transient (i.e., not-volatile) medium.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method comprising:
using at least one hardware processor for automatically:
displaying to a radiologist, using a user interface associated with the at least one hardware processor, a medical image of a patient, the medical image associated with a suspected disease of the patient and with metadata of the patient;
receiving from the radiologist, using the user interface, an annotation for the medical image and subsequent changes to the annotation, wherein the annotation describes, using certain nomenclature, an object seen by the radiologist in the medical image;
in real time with the receipt of the annotation and the changes to the annotation:
(i) using the annotation, the changes to the annotation, and the medical image, as search queries issued to a medical image database,
(ii) retrieving, from the medical image database, multiple results of the search queries, wherein the multiple results comprise (a) multiple other medical images similar to the medical image, or multiple other medical images having associated annotations that are textually-similar to the annotation or to the changes to the annotation, respectively, and (b) multiple other annotations associated with the multiple other medical images, wherein the multiple other annotations use different nomenclature than the certain nomenclature to describe objects depicted in the multiple other medical images, the objects being similar to the object in the medical image,
(iii) ranking the multiple results by at least one of:
a score which is a function of a medical severity difference between the annotation or the changes to the annotation, respectively, and each of the multiple other medical annotations, and
a score which is a function of a visual difference between the object in the medical image and each of the objects in the multiple other medical images, wherein the visual difference is calculated across at least some of the following characteristics: shape, margin, density, and distribution,
(iv) based on the ranking, determining which of the multiple other medical images and the multiple other medical annotations should be displayed to the radiologist, and displaying the determined other medical images and other medical annotations on the user interface, to enable the radiologist to compare: (a) the object in the medical image with the objects in the other medical images, and (b) the annotation or the changes to the annotation, respectively, with the multiple other annotations,
such that, as the radiologist changes the annotation, the display of the other medical images and the other annotations changes interactively, in real time with the changes to the annotation;
receiving from the radiologist, using the user interface, at least one new annotation for the medical image, wherein the at least one new annotation is consistent with the nomenclature of at least one of the multiple other annotations; and
storing the at least one new annotation in the medical image database, in association with the medical image.

2. The method according to claim 1, wherein the medical image database is incorporated into at least one of a picture archiving and communication system (PACS) system, and a radiological information system (RIS).

3. The method according to claim 1, wherein at least one of the search queries is a Digital Imaging and Communications in Medicine (DICOM) search query, and the retrieving is performed using a DICOM retrieve command.

4. The method according to claim 1, wherein the ranking of the multiple results is by both scores, and is given, for each of the multiple other medical annotations and objects in each of the multiple other medical images, by:

$$\frac{\sum_i \text{severity}(x_i)}{\sum_i \text{visual}(x_i)},$$

wherein:
$\Sigma_i$ severity($x_i$) is a sum of medical severity differences across at least some of said characteristics (i) of the respective other medical annotation; and
$\Sigma_i$ visual($x_i$) is a sum of visual differences across at least some of said characteristics (i) of the respective object in the respective other medical image.

5. The method according to claim 1, wherein:
the score which is a function of the medical severity difference is based on a table of predefined numerical distance values between said characteristics of the received annotation and corresponding said characteristics of each of the multiple other medical annotations; and
the score which is a function of the visual difference is based on a table of predefined numerical distance values between said characteristics of the object in the medical image and corresponding said characteristics of objects in each of the multiple other medical images.

6. A computer program product for automatically comparing annotations of medical images, the computer program product comprising a non-transitory computer-readable storage medium having program code embodied therewith, the program code executable by at least one hardware processor to automatically:
display to a radiologist, using a user interface associated with the at least one hardware processor, a medical image of a patient, the medical image associated with a suspected disease of the patient and with metadata of the patient;
receive from the radiologist, using the user interface, an annotation for the medical image and subsequent changes to the annotation, wherein the annotation describes, using certain nomenclature, an object seen by the radiologist in the medical image;
in real time with the receipt of the annotation and the changes to the annotation:
(i) use the annotation, the changes to the annotation, and the medical image, as search queries issued to a medical image database,
(ii) retrieve, from the medical image database, multiple results of the search queries, wherein the multiple results comprise (a) multiple other medical images similar to the medical image, or multiple other medical images having associated annotations that are textually-similar to the annotation or to the changes to the annotation, and (b) multiple other annotations associated with the multiple other medical images, wherein the multiple other annotations use different nomenclature than the certain nomenclature to describe objects depicted in the multiple other medical images, the objects being similar to the object in the medical image, (iii) rank the multiple results by at least one of:
a score which is a function of a medical severity difference between the annotation or the changes to the annotation, respectively, and each of the multiple other medical annotations, and
a score which is a function of a visual difference between the object in the medical image and each of the objects in the multiple other medical images, wherein the visual difference is calculated across at least some of the following characteristics: shape, margin, density, and distribution, (iv) based on the ranking, determine which of the multiple other medical images and the multiple other medical annotations should be displayed to the radiologist, and display the determined other medical images and other medical annotations on the user interface, to enable the radiologist to compare: (a) the object in the medical image with the objects in the other medical images, and (b) the annotation or the changes to the annotation, respectively, with the multiple other annotations, such that, as the radiologist changes the annotation, the display of the other medical images and the other annotations changes interactively, in real time with the changes to the annotation;

receive from the radiologist, using the user interface, at least one new annotation for the medical image, wherein the at least one new annotation is consistent with the nomenclature of at least one of the multiple other annotations; and store the at least one new annotation in the medical image database, in association with the medical image.

7. The computer program product according to claim 6, wherein the medical image database is incorporated into at least one of a picture archiving and communication system (PACS) system, and a radiological information system (RIS).

8. The computer program product according to claim 6, wherein at least one of the search queries is a Digital Imaging and Communications in Medicine (DICOM) search query, and the retrieving is performed using a DICOM retrieve command.

9. A system comprising:
(i) a non-transitory computer-readable storage medium having program code embodied therewith, the program code executable by at least one hardware processor to:
display to a radiologist, using a user interface associated with the at least one hardware processor, a medical image of a patient, the medical image associated with a suspected disease of the patient and with metadata of the patient;
receive from the radiologist, using the user interface, an annotation for the medical image and subsequent changes to the annotation, wherein the annotation describes, using certain nomenclature, an object seen by the radiologist in the medical image;
in real time with the receipt of the annotation and the changes to the annotation:
(i) use the annotation, the changes to the annotation, and the medical image, as search queries issued to a medical image database, (ii) retrieve, from the medical image database, multiple results of the search queries, wherein the multiple results comprise (a) multiple other medical images similar to the medical image, or multiple other medical images having associated annotations that are textually-similar to the annotation or to the changes to the annotation, and (b) multiple other annotations associated with the multiple other medical images, wherein the multiple other annotations use different nomenclature than the certain nomenclature to describe objects depicted in the multiple other medical images, the objects being similar to the objects in the medical image, (iii) rank the multiple results by at least one of:
a score which is a function of a medical severity difference between the annotation or the changes to the annotation, respectively, and each of the multiple other medical annotations, and
a score which is a function of a visual difference between the object in the medical image and each of the objects in the multiple other medical images, wherein the visual difference is calculated across at least some of the following characteristics: shape, margin, density, and distribution, (iv) based on the ranking, determine which of the multiple other medical images and the multiple other medical annotations should be displayed to the radiologist, and display the determined other medical images and other medical annotations on the user interface, to enable the radiologist to compare: (a) the object in the medical image with the objects in the other medical images, and (b) the annotation or the changes to the annotation, respectively, with the multiple other annotations, such that, as the radiologist changes the annotation, the display of the other medical images and the other annotations changes interactively, in real time with the changes to the annotation;

receive from the radiologist, using the user interface, at least one new annotation for the medical image, wherein the at least one new annotation is consistent with the nomenclature of at least one of the multiple other annotations; and store the at least one new annotation in the medical image database, in association with the medical image; and (ii) at least one hardware processor configured to execute the program code.

10. The system according to claim 9, wherein the medical image database is incorporated into at least one of a picture archiving and communication system (PACS) system, and a radiological information system (RIS).

11. The system according to claim 9, wherein at least one of the search queries is a Digital Imaging and Communications in Medicine (DICOM) search query, and the retrieving is performed using a DICOM retrieve command.

12. The system according to claim 9, wherein the ranking of the multiple results is by both scores, and is given, for each of the multiple other medical annotations and objects in each of the multiple other medical images, by:

$$\frac{\sum_i \text{severity}(x_i)}{\sum_i \text{visual}(x_i)},$$

wherein:

$\Sigma_i$ severity($x_i$) is a sum of medical severity differences across at least some of said characteristics (i) of the respective other medical annotation; and $\Sigma_i$ visual($x_i$) is a sum of visual differences across at least some of said characteristics (i) of the respective object in the respective other medical image.

13. The system according to claim 9, wherein:

the score which is a function of the medical severity difference is based on a table of predefined numerical distance values between said characteristics of the received annotation and corresponding said characteristics of each of the multiple other medical annotations; and the score which is a function of the visual difference is based on a table of predefined numerical distance values between said characteristics of the object in the medical image and corresponding said characteristics of objects in each of the multiple other medical images.

* * * * *